United States Patent
Amon et al.

(10) Patent No.: US 10,576,203 B2
(45) Date of Patent: Mar. 3, 2020

(54) METHOD FOR CALIBRATING AN INFUSION DEVICE

(71) Applicant: Fresenius Vial SAS, Brézins (FR)

(72) Inventors: Barbara Amon, Idstein (DE); Michael Becker, Knittlingen (DE)

(73) Assignee: Fresenius Vial SAS, Brézins (FR)

(*) Notice: Subject to any disclaimer, the term of this patent is extended or adjusted under 35 U.S.C. 154(b) by 337 days.

(21) Appl. No.: 15/551,712

(22) PCT Filed: Mar. 2, 2016

(86) PCT No.: PCT/EP2016/054347
§ 371 (c)(1),
(2) Date: Aug. 17, 2017

(87) PCT Pub. No.: WO2016/146382
PCT Pub. Date: Sep. 22, 2016

(65) Prior Publication Data
US 2018/0028751 A1 Feb. 1, 2018

(30) Foreign Application Priority Data
Mar. 17, 2015 (EP) .................................. 15290075

(51) Int. Cl.
*A61M 5/172* (2006.01)
*A61M 5/142* (2006.01)
(Continued)

(52) U.S. Cl.
CPC ........ *A61M 5/172* (2013.01); *A61M 5/14228* (2013.01); *A61M 5/14232* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 2011/0034900 A1* | 2/2011 | Yodfat | A61M 5/14232 604/500 |
| 2012/0207635 A1 | 8/2012 | Becker | |
| 2013/0020237 A1* | 1/2013 | Wilt | A61M 1/1037 210/85 |

FOREIGN PATENT DOCUMENTS

| WO | WO 98/31935 | 7/1998 |
|---|---|---|
| WO | WO 2009/026060 A2 | 2/2009 |

(Continued)

OTHER PUBLICATIONS

International Search Report and Written Opinion, counterpart PCT Appl. No. PCT/EP2016/054347, 14 pages (dated May 17, 2016).

*Primary Examiner* — Kami A Bosworth
*Assistant Examiner* — Leah J Swanson
(74) *Attorney, Agent, or Firm* — Cook Alex Ltd.

(57) ABSTRACT

An infusion device includes a pump device having a housing and a flexible wall section together forming a channel extending along a channel length between first and second ends. An actuation device locally depresses the flexible wall section in a vertical direction, and is displaceable along the vertical direction. To pump a fluid through the channel, the actuation device is actuated to depress the flexible wall section at a depression location, the depression location during one pump cycle moving along the channel length. To calibrate the infusion device, the position of the actuation device along the vertical direction during one pump cycle is measured to obtain a measured profile, a difference between the measured profile and a prestored nominal profile is formed to obtain a difference profile, and from the difference profile a characteristic value for correcting and/or checking the pump operation of the infusion device is calculated.

14 Claims, 8 Drawing Sheets

(51) Int. Cl.
  *F04B 43/14* (2006.01)
  *A61M 5/14* (2006.01)
  *F04B 43/12* (2006.01)
  *F04B 51/00* (2006.01)

(52) U.S. Cl.
  CPC ........... *F04B 51/00* (2013.01); *A61M 5/1413* (2013.01); *A61M 2205/18* (2013.01); *A61M 2205/3327* (2013.01); *A61M 2205/3334* (2013.01); *A61M 2205/3351* (2013.01); *A61M 2205/3355* (2013.01); *A61M 2205/3379* (2013.01); *A61M 2205/702* (2013.01); *F04B 43/1207* (2013.01); *F04B 43/14* (2013.01)

(56) References Cited

FOREIGN PATENT DOCUMENTS

| WO | WO 2009/113075 A1 | 9/2009 |
| WO | WO 2012/049260 A2 | 4/2012 |

\* cited by examiner

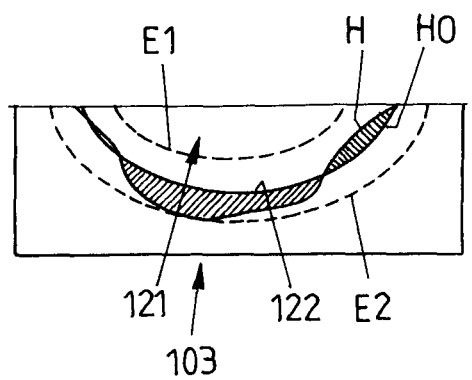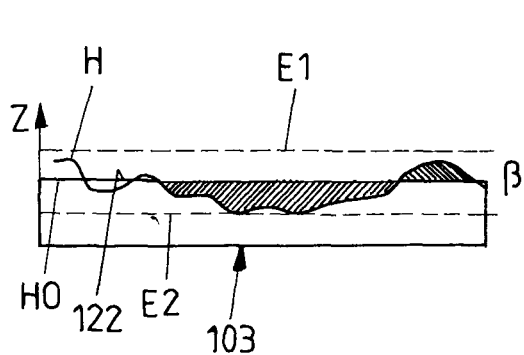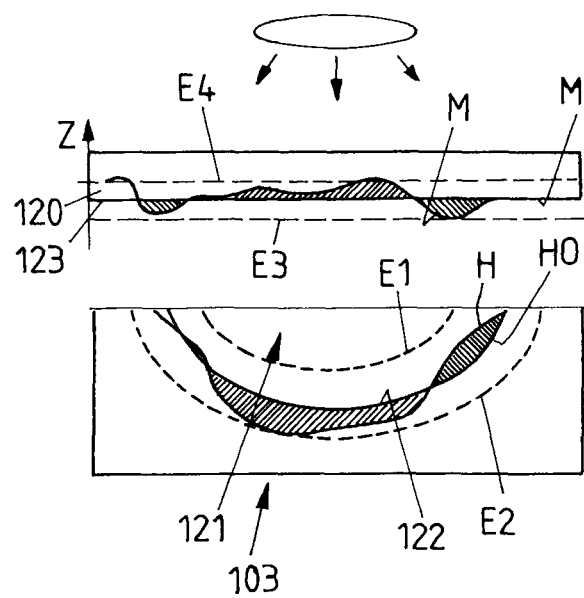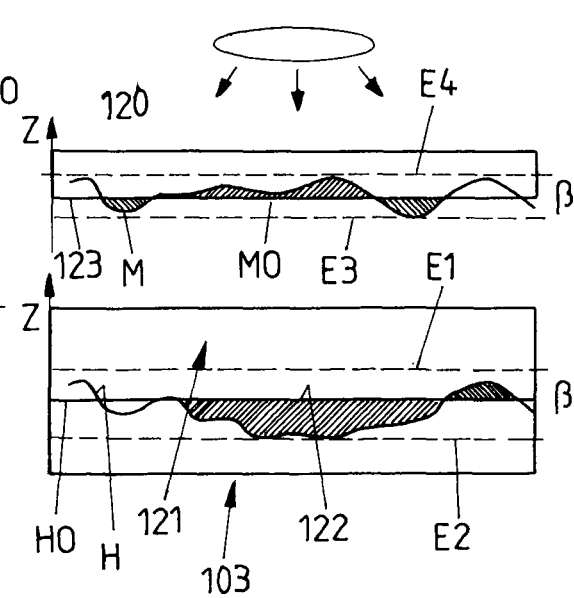

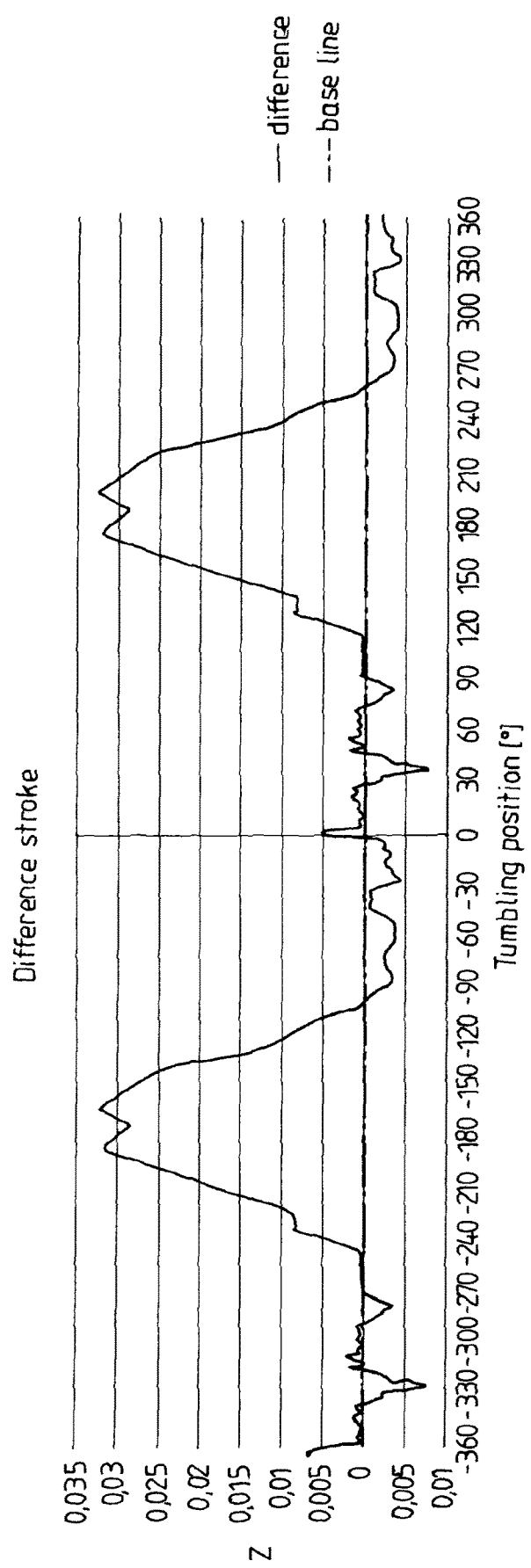

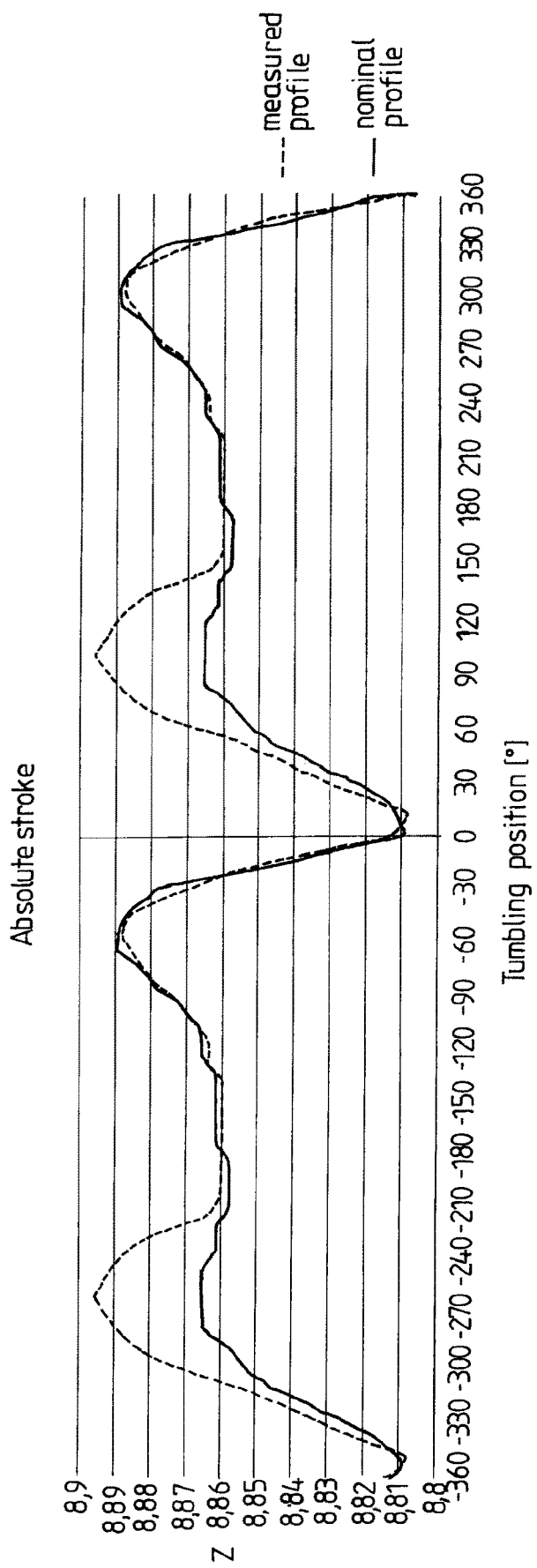

METHOD FOR CALIBRATING AN INFUSION DEVICE

The present application is a U.S. National Stage of PCT International Patent Application No. PCT/EP2016/054347, filed Mar. 2, 2016, which claims priority to EP Application No. 15290075.9, filed Mar. 17, 2015, both of which are hereby incorporated herein by reference.

The invention relates to a method for calibrating an infusion device according to the preamble of claim 1 and to an infusion device.

An infusion device of this kind is constituted as a peristaltic (volumetric) infusion pump having a pump device and a pump actuation mechanism acting onto the pump device in a peristaltic fashion in order to pump a fluid through the pump device. The pump device has a housing part and a flexible wall section which together form a pump channel through which a fluid shall be pumped. The pump channel herein has a first end serving as inlet for the fluid and a second end serving as outlet for the fluid, wherein the pump channel extends along a channel length between the first end and the second end. The pump actuation mechanism in turn is constituted to act onto the pump device for performing a pumping action and for this comprises an actuation device for acting onto the flexible wall section along the channel length of the pump channel. By means of the actuation device the flexible wall section shall locally be depressed in a vertical direction in order to peristaltically pump a fluid through the pump channel.

The pump device may, for example, have the shape of a disposable pump module which can be attached to a suitable reception opening of the infusion device. By attaching the pump module to the reception opening, it is brought into engagement with the actuation device of the pump actuation mechanism such that, in operation of the infusion device, the actuation device may act onto the flexible wall section in order to pump a fluid through the pump channel.

In order to allow a reliable interaction of the actuation device with the flexible wall section the actuation device is arranged displaceably with respect to a housing section of the pump actuation mechanism along the vertical direction. By pretensioning the actuation device towards the flexible wall section it can be ensured that the actuation device is in suitable abutment with the flexible wall section when the pump device is arranged on the infusion device.

Under the control of a control device the pump actuation mechanism, during operation of the infusion device, is actuated to pump a fluid through the pump channel. During operation the actuation device hence depresses the flexible wall section at a depression location, wherein by actuating the actuation device the depression location moves along the channel length of the pump channel and in this way peristaltically pumps a fluid through the pump channel.

Generally, during one pump cycle the infusion device pumps a defined volume of fluid, denoted as "stroke volume", through the pump channel. The stroke volume is defined by the volume of the pump channel and can be measured for example by measuring the volume of fluid which flows out of the pump channel during one pump cycle.

In a known peristaltic pump having a tumbling actuation device, the stroke volume is for example defined by the volume of the pump channel in a position of the tumbling actuation device in which it closes both the inlet at the first end of the pump channel and the outlet at the second end of the pump channel.

Typically, a pump channel of a defined design has a nominal stroke volume whose value is stored in the control device of the infusion device. According to the stored stroke volume value, operational parameters of the infusion device such as the infusion rate can be determined and set. For example, if a user enters a specific infusion rate at which a fluid shall be infused into a patient during an infusion operation, the control device sets the speed of the actuation device taking the stroke volume into account in order to achieve the desired infusion rate (volume per time).

As said, the pump device may be constituted as a disposable pump module which for example is fabricated at least partially from plastics. Naturally, when fabricating a pump device of this kind with a pump channel formed therein, tolerances will occur which have an influence on the shape of the pump channel and its real volume. The real stroke volume may hence differ from the nominal stroke volume value as it has been set and stored in the control device. Thus, when setting and controlling a pump operation using the nominal stroke volume value, this may be inaccurate and may for example lead to an inaccurate infusion rate, i.e., the actual, real infusion rate achieved during the pump operation may differ from the desired infusion rate which was meant to be set.

There hence is a desire to be able to correct for effects of tolerances in the shape of the pump channel.

An infusion device as generally concerned herein is for example described in WO 2012/049260 A2.

It is an object of the instant invention to provide a method for calibrating an infusion device which in a reliable manner allows for taking tolerances within the actual shape of a pump channel into account for controlling an infusion operation.

This object is achieved by means of a method according to the features of claim 1.

Herein, the method comprises the following steps:
measuring the position of the actuation device along the vertical direction during one pump cycle to obtain a measured profile,
forming a difference between the measured profile and a nominal profile prestored in the control device to obtain a difference profile, and
calculating, from the difference profile, a characteristic value for correcting and/or checking the pump operation of the infusion device.

Accordingly, a method for calibrating an infusion device is provided which allows to correct or at least check for deviations of an actual stroke volume from a prestored, nominal stroke volume value. The method herein is based on the idea that, during one pump cycle, the vertical position of the actuation device, for example a tumbling disc, will change by at least some degree, wherein during periodic actuation of the actuation device for performing multiple pump cycles the displacement periodically is repeated. If the pump device has an ideal shape according to its definition, the displacement of the actuation device in the vertical direction during one pump cycle will adhere to a characteristic profile. However, since any pump device can be manufactured only within finite margins of tolerance, this ideal profile will realistically not be obtained, but an actual displacement profile of the actuation device during one pump cycle will differ from the nominal profile. If a nominal profile is predetermined and prestored in the control device and, during one pump cycle of operation, the displacement of the actuation device in the vertical direction is measured to obtain a measure profile, a difference profile can be calculated by forming the difference between the nominal profile and the measured profile. From this difference profile, then, conclusions can be drawn with respect to the shape tolerances of the pump channel of the pump device and, in particular, with respect to a real stroke volume of the pump channel in comparison to a nominal stroke volume value.

The measured profile is measured during one pump cycle. It hence is represented by the vertical position of the actuation device along the channel length over one pump cycle. Likewise, the nominal profile is represented by the nominal vertical position of the actuation device over the channel length.

From the difference profile, a characteristic value may be derived. The characteristic value may for example be calculated according to the integral of the difference profile obtained from the measured profile during one pump cycle.

The characteristic value may be used in different ways to correct and/or check the operation of an infusion device.

In a first embodiment, the characteristic value may simply be used to check for too large deviations of the actual pump channel shape from a nominal pump channel shape. I.e., if the difference between the measured profile and the nominal profile becomes too large, this may be recognized and an alarm may be issued, possibly leading to the stopping of an infusion operation.

In a second embodiment, the characteristic value may be used to correct a nominal stroke volume value which is stored in the control device to obtain a corrected stroke volume value. The operation of the infusion device may then be controlled using the corrected stroke volume value in order to, for example set an infusion rate in a more accurate fashion.

Hence, by determining and using the characteristic value an infusion device may be calibrated. This calibration may take place once in a specific calibration routine prior to the actual operation of the infusion device. In this case, in the calibration routine the corrected stroke volume value is determined and stored in the control device and, during subsequent operation of the infusion device, is used to set operational parameters of the infusion device such as in particular the infusion rate.

It, however, is also conceivable that a correction of this kind is used during operation of the infusion device, e.g., during performing an actual infusion operation. For example, a measured profile could be determined during every pump cycle and may be used to update the characteristic value, which may then be used to update the corrected stroke volume value.

For correcting the nominal stroke volume value, the characteristic value is used to calculate a correction value. The correction value may then be added or subtracted from the nominal stroke volume value in order to obtain the corrected stroke volume value. The correction value may for example be obtained by multiplying the characteristic value with a translation factor, wherein the translation factor may be prestored in the control device.

The translation factor can for example initially be determined and set once at the site of the manufacturer by performing a pump operation and by determining a measured profile and a difference profile for a pump cycle. In addition, it may be determined by measuring the actual stroke volume to what stroke volume deviation a characteristic value derived from the difference profile relates. In this way the characteristic value derived from the difference profile may be calibrated by setting it in relation to an actual stroke volume deviation, i.e., a deviation of the actual stroke volume from the nominal stroke volume.

The actual stroke volume may for example be determined by having the infusion device perform one hundred pump cycles and measure the volume of fluid which has been pumped in those one hundred pump cycles. The stroke volume is then determined by dividing the measured volume by one hundred.

In order to set the obtained measured profile during one pump cycle and the nominal profile in relation to each other, the nominal profile and/or the measured profile beneficially are normalized prior to forming the difference. In particular, the nominal profile and the measured profile may be set in relation to each other by drawing them to a common reference. I.e., the nominal profile and the measured profile may be set to be equal at a point along the channel length of the pump channel, for example at 0° (for a circular pump channel in which the 0° position relates to a position of the actuation device in which both the inlet and the outlet of the pump channel are closed off).

The actuation device for example is constituted as a tumbling device performing a tumbling movement for acting onto the flexible wall section. The actuation device hence does not rotate during actuation, but in a tumbling fashion acts onto the flexible wall section, for example a membrane arranged on the housing part of the pump device. The depression location hence in a rotating fashion moves along the pump channel, without the actuation device actually rotating.

Beneficially, the actuation device is elastically pretensioned towards the flexible wall section. The actuation device, in an operational state of the infusion device, hence abuts the flexible wall section under a pretension. For this, for example a mechanical spring element may act in-between the actuation device and the stationary housing section of the pump actuation mechanism such that the actuation device is tensioned towards the flexible wall section.

This may beneficially lead to a pre-loading of the flexible wall section in that in any case the actuation device abuts the flexible wall section along the entire channel length. Herein, according to the position of the actuation device the flexible wall section only locally depresses the flexible wall section such that the height of the pump channel at this depression location is reduced to a minimum and the pump channel at this location is squeezed off. However, also at other locations along the pump channel the actuation device abuts the flexible wall section such that the flexible wall section is preloaded in the vertical direction along the entire channel length.

The pump channel advantageously is formed by a trench in the housing part of the pump device. The housing part may be made for example of a rigid plastic material. The flexible wall section in turn may for example be formed by a membrane attached to the housing part, or by a thin wall section formed in one piece with the housing part, for example using a two-component moulding technology and having a sufficient elasticity.

The pump channel may for example extend along an arch of a circle, wherein the circle is not closed, but interrupted to separate the inlet at the first end of the pump channel from the outlet at the second end of the pump channel. The pump channel may for example extend along a plane transverse to the vertical direction. The pump channel hence is laid out in a horizontal plane, and the flexible wall section of the pump channel is depressed vertically to that horizontal plane in order to perform a peristaltic pump action on the pump channel.

The object is also achieved by an infusion device. The infusion device comprises a pump device having a housing part and a flexible wall section together forming a pump channel through which a fluid is to be pumped, wherein the pump channel has a first end as inlet for a fluid and a second end as outlet for a fluid, wherein the pump channel extends along a channel length between the first end and the second end on the pump device. The infusion device furthermore comprises a pump actuation mechanism having an actuation device for acting onto the flexible wall section along the channel length of the pump channel for locally depressing the flexible wall section in a vertical direction in order to pump a fluid through a pump channel, the actuation device being displaceable with respect to a housing section of the pump actuation mechanism along the vertical direction. A control device is provided to control the operation of the pump actuation mechanism, wherein, for pumping a fluid through the pump channel, the actuation device is actuatable to depress the flexible wall section at a depression location such that during one pump cycle the depression location moves along the channel length of the pump channel.

Herein, the control device is constituted to form a difference between a measured profile, obtained by measuring the position of the actuation device along the vertical direction during one pump cycle, and a nominal profile prestored in the control device to obtain a difference profile, wherein the control device furthermore is constituted to calculate, from the difference profile, a characteristic value for correcting and/or checking the pump operation of the infusion device.

The advantages and advantageous embodiments described above for the method equally apply also to the infusion device as set forth above, such that it shall be referred to the above.

In order to be able to measure a vertical position of the actuation device, the infusion device beneficially comprises a suitable sensor device which is constituted to measure the position of the actuation device along the vertical direction with respect to a reference position. Such sensor device may for example be an optical sensor or any other sensor which is suitable to measure displacements.

The idea underlying the invention shall subsequently be described in more detail with regard to the embodiments shown in the figures. Herein, FIG. 1 shows a top view of an embodiment of a pump device in the shape of a pump module;

FIG. 5A shows a sectional view of a pump channel formed in a housing part of the pump device, the sectional view corresponding to a portion of the sectional view of FIG. 2;

FIG. 5B shows a sectional, schematic view along the length of the pump channel;

FIG. 6A shows the view of FIG. 5A, including a flexible wall section in the shape of a membrane;

FIG. 6B shows the view of FIG. 5B, including a flexible wall section in the shape of a membrane;

FIG. 7B shows a difference profile obtained by forming the difference between the measured profile and the nominal profile;

FIG. 8A shows another measured profile together with a nominal profile; and

Figure 1:
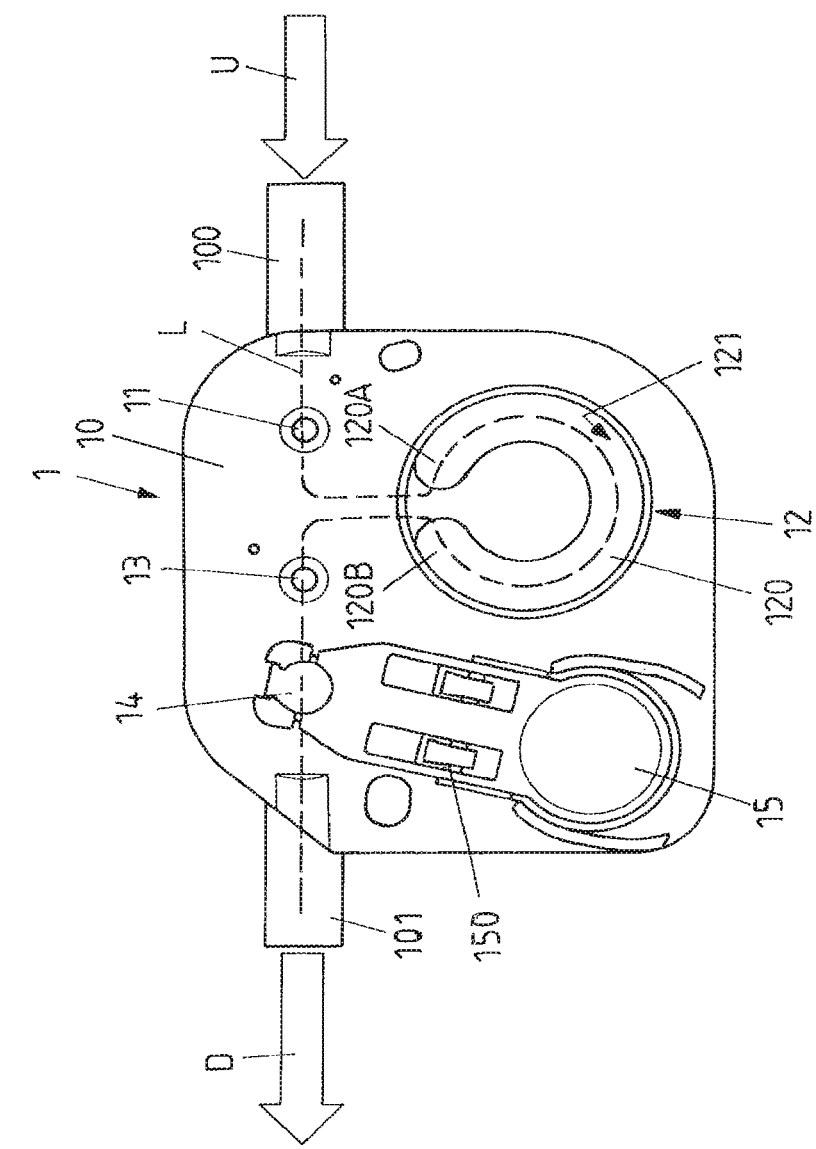

FIG. 1 shows a schematic top view of a pump device 1 in the shape of a pump module which may be constituted as a disposable piece and may be part of an infusion set to be attached to an infusion device in the shape of a peristaltic infusion pump. The pump device 1 comprises a housing 10 having an inlet 100 and an outlet 101. The inlet 100 and the outlet 101 may be connected to a suitable tubing forming an infusion line such that an upstream flow U may enter the pump device 1 at the inlet 100 and a downstream flow D may exit the pump device 1 through the outlet 101.

Within the pump device 1 a flow path L is defined through which a fluid passes the pump device 1. Along the flow path L, as viewed from the inlet 100, a fluid flow first passes a pressure sensing location 11, then through an end 120A enters a pump channel 121 of a pump section 12 and exits the pump channel 121 through an end 120B. The fluid flow then passes another pressure sensing location 13 and flows through a valve device 14 which by means of an actuation handle 115 arranged pivotably about pivot axis 150 on the housing 10 may be actuated to selectively open or close the flow path L.

At the pressure sensing locations 11, 13 thin, flexible wall sections on the housing 10 may be provided such that pressure sensors of the infusion device are enabled to sense the pressure at the pressure sensing locations 11, 13 within the flow path L.

In the embodiment of the pump device 1 according to FIG. 1, the pump section 12 has a pump channel 121 having the shape of an arch of a circle. The circle is not closed such that the ends 120A, 120B are separated from one another.

Figure 2:
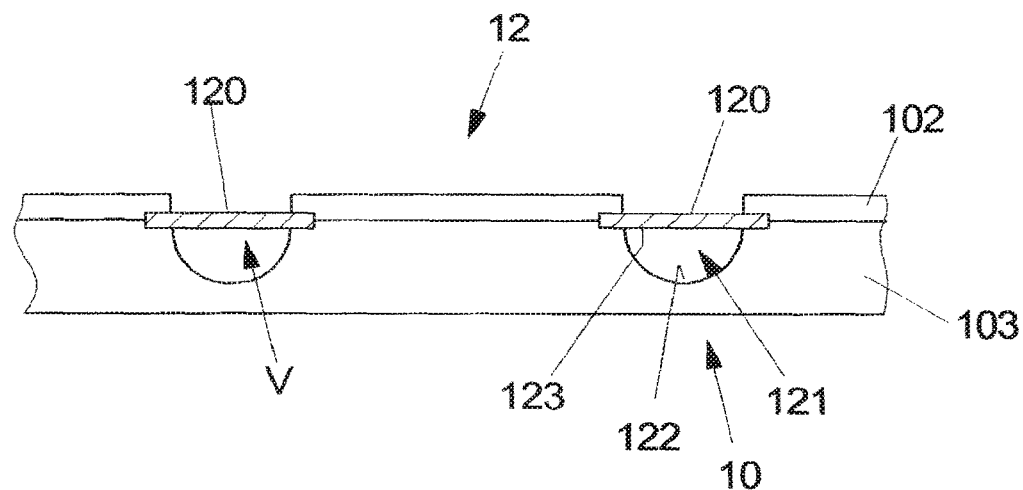
FIG. 2 shows a schematic cross-sectional view along line I-I of FIG. 1.

As schematically shown in FIG. 2, within the pump section 12 the pump channel 121 is formed by a trench in a housing part 103 of the housing 10 of the pump device 1. The pump channel 121, towards the outside, is covered by a flexible wall section 120 in the shape of a membrane, which is held between the housing part 103 and another, top housing part 102. The flexible wall section 120 may be glued or welded to the housing part 103 or may be held in-between the housing parts 102, 103 in a clamping fashion. The flexible wall section 120 may alternatively also be formed in one piece together with the housing parts 102, 130 using for example a two-component molding technology.

Whereas the flexible wall section 120 is elastic such that it may locally be depressed in order to perform a pump action, the housing parts 102, 103 are formed as rigid pieces for example from plastics.

Figure 3:
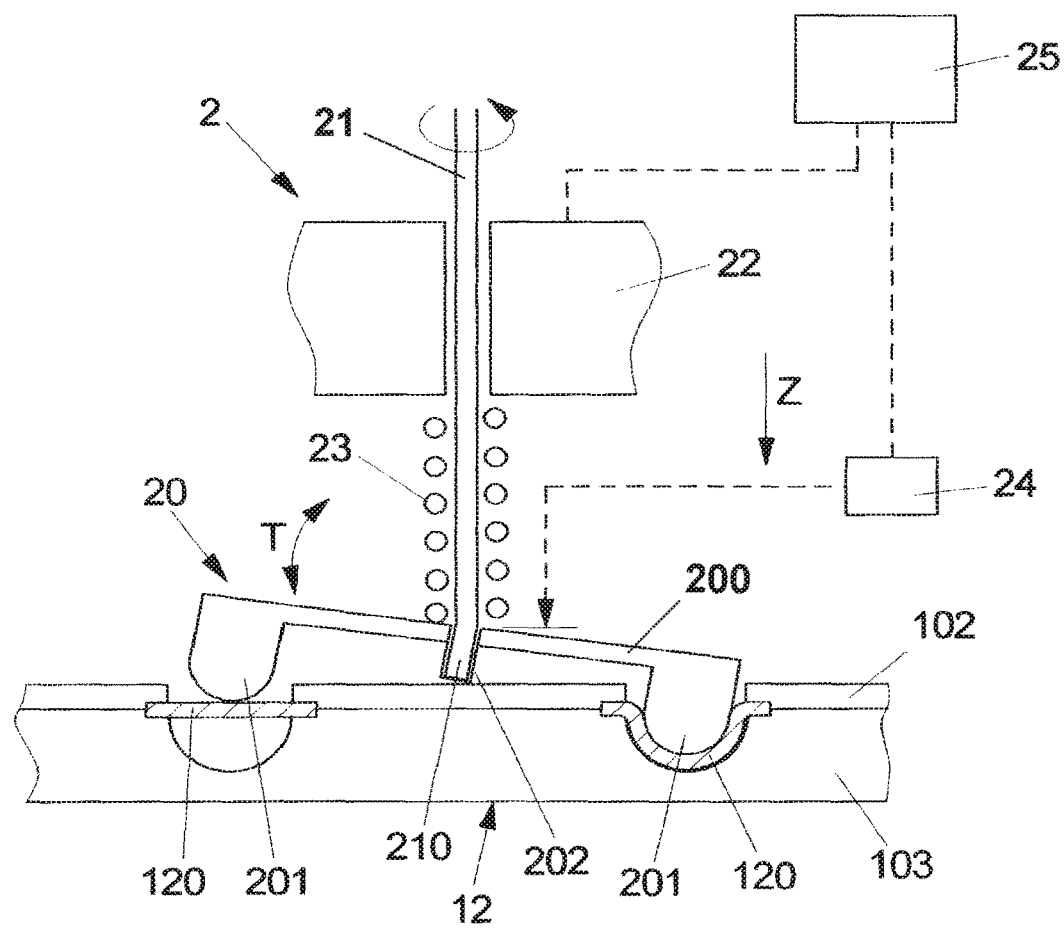
FIG. 3 shows the schematic view of FIG. 2, in interaction with a pump mechanism for pumping a fluid through a pump channel formed in the pump device.

FIG. 3 shows the pump section 12 of the pump device 1 in interaction with a pump actuation mechanism 2. The pump actuation mechanism 2, in the shown simplified embodiment, comprises an actuation device 20 in the shape of a tumbling device which has a tumbling disc 200 and an arched projection 201 projecting from the tumbling disc 200 towards the flexible wall section 120 and, along the pump channel length, forming an arch similar in shape to the arch of the pump channel 121. The tumbling device 20 is in engagement with a drive shaft 21 in that the drive shaft 21 reaches into an engagement opening 202 formed on the tumbling disc 200 via an end 210 of the drive shaft 21. The drive shaft 21 can be rotated in order to actuate the tumbling device 20 and, for example by means of a suitable bearing, is mounted on a stationary housing section 22 of the pump actuation mechanism 2.

In an operational state of the infusion device the tumbling device 20 is in abutment with the flexible wall section 120 of the pump device 1. The tumbling device 20 herein is pretensioned by means of a spring element 23 with respect to the stationary housing section 22 of the pump actuation mechanism 2 in a vertical direction Z towards the flexible wall section 120. This leads to a preloading of the flexible wall section 120, causing the tumbling device 20 to be in abutment with the flexible wall section 120 along the entire channel length of the pump channel 121 such that the flexible wall section 120 is preloaded along the channel length of the pump channel 121.

Since the tumbling device 20 is elastically pretensioned towards the flexible wall section 120, it is by at least some margin movable along the vertical direction Z with respect to the stationary housing section 22 of the pump actuation mechanism 2. During operation of the pump actuation mechanism 2 the vertical position Z of the tumbling device 20 may change with respect to the stationary housing section 22, which may be measured by means of a suitable sensor device 24.

The vertical position Z of the tumbling device 20 may for example be measured at a central position of the tumbling device 20 not affected by the tumbling movement T of the tumbling device 20, but in principle may be measured at any location on the tumbling device 20.

A control device 25 is provided which controls the infusion operation and the actuation of the pump actuation mechanism 2. The control device 25 also is constituted to evaluate sensing data provided by the sensor device 24.

Figure 4:
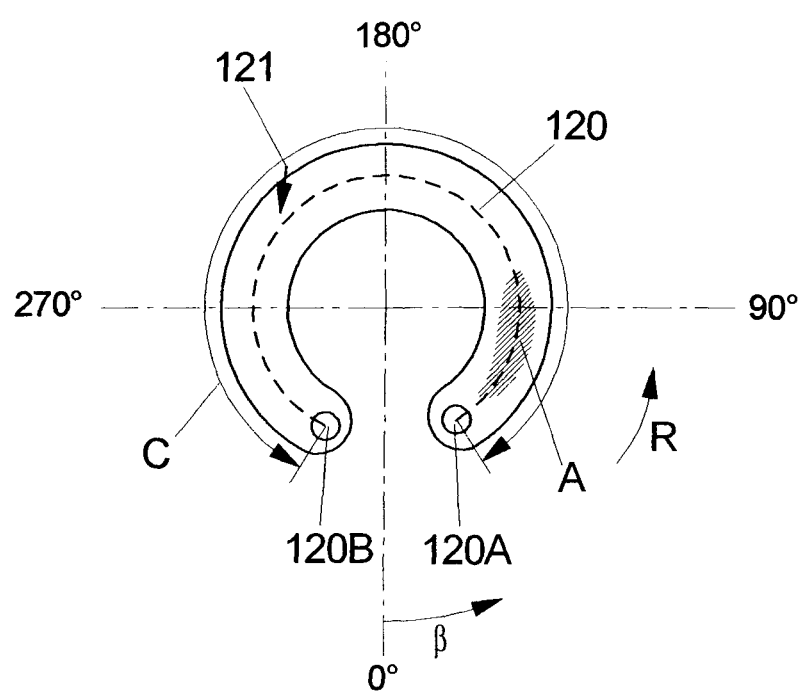
FIG. 4 shows a separate top view of a pump channel.

FIG. 4 schematically shows the pump channel 121 with its flexible wall section 120 in a separate view. Fluid may enter the pump channel 121 via a first end 120A and, during one pump cycle, is pumped from the first end 120A towards a second end 120B by the tumbling actuation of the tumbling device 20. If the tumbling device 20 herein as at a position corresponding to an angle of 0°, it closes the pump channel 121 both at its inlet end 120A and at its outlet end 120B. If, during one pump cycle, the tumbling device 20 is actuated, it depresses the flexible wall section 120 at a depression location A which actually corresponds to an area at which the flexible wall section 120 is depressed towards a floor 122 (see FIG. 2) of the pump channel 121 such that, as is shown in FIG. 3, the pump channel 121 is locally closed by squeezing the flexible wall section 120 towards the floor 122 of the pump channel 121. As the tumbling device 20 is further actuated during one pump cycle, the depression location A moves along the channel length C of the pump channel 121 in a tumbling direction R such that fluid peristaltically is pumped through the pump channel 121.

The pump channel 121 has a defined stroke volume V (see FIG. 2). This stroke volume V corresponds to the volume of the pump channel 121 at the 0° position of the tumbling device 20, i.e., at the position of the tumbling device 20 at which the pump channel 121 is closed at both ends 120A, 120B. The stroke volume V corresponds to the volume of the fluid that is pumped through the pump channel 121 during one pump cycle, i.e., during one tumbling revolution of the tumbling device 20.

The stroke volume V nominal is defined by the shape of the trench in the housing part 103. This shape has a defined design such that, according to the defined design, the stroke volume V has a nominal value, in the following denoted as "nominal stroke volume value".

However, the pump device 1 has tolerances and can be fabricated only with finite accuracy. The shape of the floor 122 of the pump channel 121 in the housing part 103 therefore is subject to tolerances. Just as well, the shape of the flexible wall section 120 in particular at a side 123 facing into the pump channel 121 is subject to tolerances.

This is illustrated in FIGS. 5A, 5B and 6A, 6B.

FIG. 5A shows a cross-sectional view of the trench formed in the housing part 103 corresponding for example to the trench portion as shown on the right in the schematic view of FIG. 2. FIG. 5B, in contrast, shows a sectional view along the dashed line of FIG. 4, i.e., along a central line of the pump channel 121 along its pump channel length C.

FIG. 6A, 6B show the views of FIG. 5A, 5B, but together with the flexible wall section 120.

At its floor 122, the pump channel 121 normally has the shape as indicated by the curve H0. However, realistically and due to tolerances, the floor 122 has the shape as indicated by the curve H, which may lie above or below the nominal curve H0. This curve H may lie within envelope lines E1, E2 defined by a maximum permissible tolerance as defined during fabrication.

Likewise, the flexible wall section 120 at its side 123 facing the pump channel 121 may normally have the shape as indicated by the curve M0, but realistically and due to tolerances may more look like the shape as illustrated by the curve M. The realistic shape according to the curve M herein may be bound by envelope lines E3, E4.

Whereas some of the tolerances may in effect cancel each other out with regard to their effect on the stroke volume V, over the entire channel length C (see FIG. 4) a residual effect may result which may have an impact on the stroke volume V. In particular, due to tolerances the actual, real stroke volume V may differ from the nominal stroke volume value as defined by the nominal design and shape of the pump device 1.

This may have an impact on the pump operation, since typically operational parameters such as the infusion rate are set according to the nominal stroke volume value. Such settings hence may be inaccurate if the nominal stroke volume value differs from the real stroke volume V.

There hence is provided a method which allows identifying deviations of the real pump channel shape from a nominal pump channel shape and its impact on for example the stroke volume.

Figure 7A:
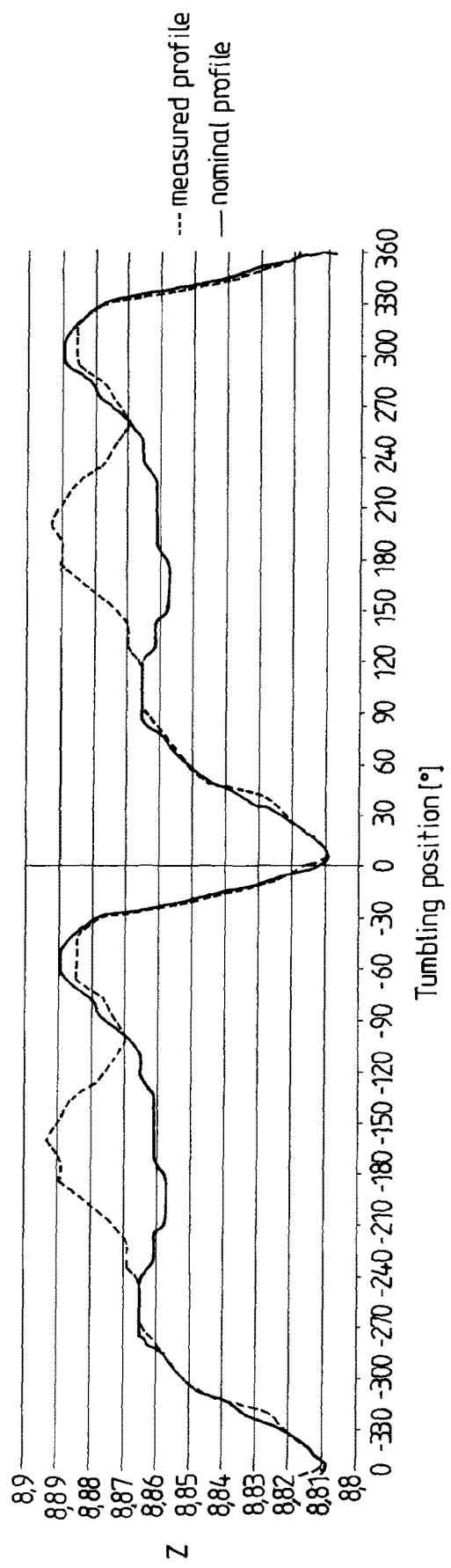
FIG. 7A shows a measured profile and a nominal profile.

As is shown in FIG. 7A, during one pump cycle the vertical position Z of the tumbling device 20 can be measured to obtain a measured profile (dashed line in FIG. 7A) which can be compared to a nominal profile which is prestored in the control device 25 of the infusion device (solid line in FIG. 7A).

The nominal profile may be obtained for example once at the site of the manufacturer for a sample pump device which is fabricated as accurate as possible and according to which the infusion device initially by the manufacturer is calibrated. For this sample pump device (also denoted as master pump device) the nominal profile can be measured and stored and it can also be measured what actual stroke volume the sample pump device has in order to set this stroke volume as the nominal stroke volume value in the control device 25 of the infusion device.

If later on the infusion device is to be used in connection with a pump device 1, for example a disposable pump device, of the same kind, but subject to tolerances, the measured profile can be measured for this actual pump device 1 to be used, and it can be compared to the prestored nominal profile which has been initially determined and stored by the manufacture for the master pump device.

For comparing the measured profile and the nominal profile to each other, they are normalized with respect to each other in that they are set to the same value at the 0° tumbling position of the tumbling device 20. This is visible in FIG. 7A.

Then, a difference profile as shown in FIG. 7B may be determined by subtracting the nominal profile from the measured profile. As visible from FIG. 7B the difference profile has areas below 0 and areas above 0, due to the measured profile partially lying below the nominal profile and partially lying above the nominal profile.

From the difference profile, then, a characteristic value can be determined by forming the integral of the difference profile.

According to the characteristic value the operation of the infusion device can be checked or the stroke volume value can be corrected to obtain a corrected stroke volume value, according to which operational parameters can be set.

For example, in one embodiment, the characteristic value obtained from the integral of the difference profile over one pump cycle can be compared to a threshold. If the characteristic value exceeds the threshold, an alarm may be triggered indicating that the pump device shall not be used because it has to large deviations.

In another embodiment, a correction value can be determined by multiplying the characteristic value by a translation factor which is prestored in the control device 25. The translation factor may be determined for example once initially by determining, for a pump device 1, what difference integral relates to what deviation in stroke volume. This may be done once by the manufacturer and may be stored for future use in the control device 25 by the manufacturer such that it does not need to be repeated by the later user of the infusion device.

Having obtained the correction value, the nominal stroke volume value, which is stored in the control device 25, can be corrected by adding or subtracting (depending on its sign) the correction value from the nominal stroke volume value in order to obtain a corrected stroke volume value.

For example, a nominal stroke volume value may be stored in the control device to be 20.9 µl. The correction value, determined by multiplying the characteristic value with the translation factor, can for example be determined to be −0.6315 µl. The corrected stroke volume value hence comes out to be 20.2685 µl. The deviation in the actual stroke volume hence is about 3% of the nominal stroke volume value.

Figure 8B:
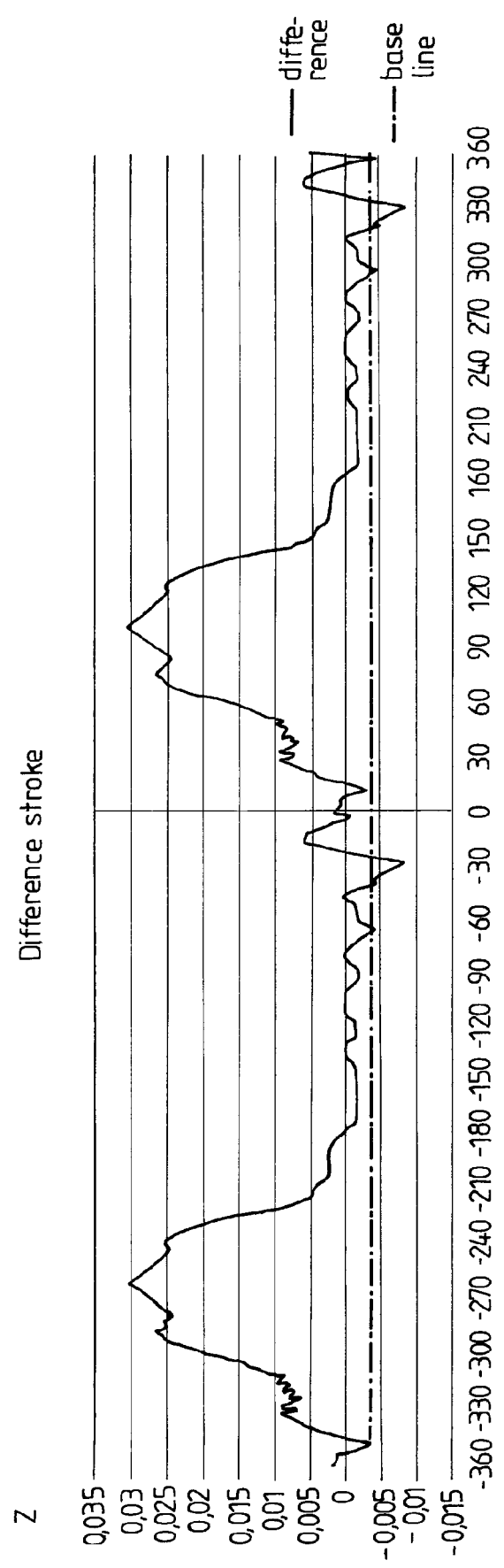
FIG. 8B shows another difference profile.

FIGS. 8A and 8B shows a different example of a measured profile in relation to a nominal profile and a difference profile obtained therefrom. The examples of FIGS. 7A, 7B and 8A, 8B have been obtained by actual measurements, wherein deviations from the defined nominal shape of the pump channel have been artificially inserted by altering the flexible wall section at its inside in a defined manner.

The idea underlying the invention is not limited to the embodiments described above, but may be implemented also in an entirely different fashion.

In particular, the invention not necessarily is limited to pump actuation mechanisms using tumbling devices, but may in principle be also applicable to pump mechanisms having rotating roller elements for acting onto a flexible wall section.

By means of the instant invention a calibration sequence is provided which allows for calibrating an infusion device to compensate for shape tolerances in a pump channel and its influences on a stroke volume. The calibration allows correcting a stroke volume and hence allows setting operational parameters of an infusion device in a more accurate manner.

LIST OF REFERENCE NUMERALS

1 Pump device
10 Housing
100 Inlet
101 Outlet
102, 103 Housing part
11 Pressure sensing location
12 Pump section
120 Flexible wall section (membrane)
120A, 120B End
121 Pump channel
122 Channel floor
123 Membrane side
13 Pressure sensing location
14 Valve device
15 Actuation handle
150 Pivot axis
2 Pump actuation mechanism
20 Actuation device (tumbling device)
200 Tumbling disc
201 Projection
202 Engagement opening
21 Drive shaft
210 End
22 Housing section
23 Spring element
24 Sensor device
25 Control device
A Area
C Channel length
D Downstream flow
E1, E2 Envelope for tolerances
H0 Nominal shape
H Real shape
L Flow path
M0 Nominal shape
M Real shape
R Tumbling direction
T Tumbling movement
U Upstream flow
Z, Z0 Position

The invention claimed is:

1. A method for calibrating an infusion device, the infusion device comprising:
 a pump device having a housing part and a flexible wall section together forming a pump channel through which a fluid is to be pumped, wherein the pump channel has a first end as an inlet for a fluid and a second end as an outlet for a fluid, wherein the pump channel extends along a channel length between the first end and the second end,
 a pump actuation mechanism having an actuation device for acting onto the flexible wall section along the channel length of the pump channel for locally depressing the flexible wall section in a vertical direction in order to pump a fluid through the pump channel, the actuation device being displaceable with respect to a housing section of the pump actuation mechanism along the vertical direction, and
 a control device to control operation of the pump actuation mechanism,
 wherein, for pumping a fluid through the pump channel, the actuation device is actuated to depress the flexible wall section at a depression location, wherein the depression location during one pump cycle moves along the channel length of the pump channel,
 the method comprising:
 measuring a position of the actuation device along the vertical direction during one pump cycle to obtain a measured profile, forming a difference between the measured profile and a nominal profile prestored in the control device to obtain a difference profile, and calculating, from the difference profile, a characteristic value for correcting and/or checking pump operation of the infusion device, wherein an integral of the difference profile along the channel length is formed to obtain the characteristic value.

2. The method according to claim 1, wherein an alarm is triggered if the characteristic value exceeds a predetermined threshold.

3. The method according to claim 1, further comprising correcting a nominal stroke volume value using the characteristic value to obtain a corrected stroke volume value.

4. The method according to claim 3, wherein the corrected stroke volume value is determined in a calibration procedure, is stored in the control device and is used during subsequent pumping operation of the infusion device.

5. The method according to claim 3, wherein a correction value is determined to correct the nominal stroke volume value by multiplying the characteristic value with a translation factor.

6. The method according to claim 5, wherein the translation factor is prestored in the control device.

7. The method according to claim 3, wherein each of the nominal stroke volume value and the corrected stroke volume values are defined by a volume of fluid pumped through the pump channel in one pump cycle.

8. The method according to claim 1, wherein the nominal profile and/or the measured profile are normalized prior to forming the difference.

9. The method according to claim 1, wherein the actuation device is a tumbling device performing a tumbling movement for acting onto the flexible wall section.

10. The method according to claim 1, wherein the actuation device is elastically pretensioned with respect to the housing section of the pump actuation mechanism along the vertical direction towards the flexible wall section.

11. The method according to claim 1, wherein the pump channel is formed by a trench in the housing part of the pump device.

12. The method according to claim 1, wherein the pump channel extends along an arc of a circle.

13. The method according to claim 1, wherein the pump channel extends along a plane transverse to the vertical direction.

14. An infusion device, comprising:

a pump device having a housing part and a flexible wall section together forming a pump channel through which a fluid is to be pumped, wherein the pump channel has a first end as an inlet for a fluid and a second end as an outlet for a fluid, wherein the pump channel extends along a channel length between the first end and the second end on the pump device, a pump actuation mechanism having an actuation device for acting onto the flexible wall section along the channel length of the pump channel for locally depressing the flexible wall section in a vertical direction in order to pump a fluid through the pump channel, the actuation device being displaceable with respect to a housing section of the pump actuation mechanism along the vertical direction, and a control device to control operation of the pump actuation mechanism, wherein, for pumping a fluid through the pump channel, the actuation device is actuatable to depress the flexible wall section at a depression location such that during one pump cycle the depression location moves along the channel length of the pump channel, wherein the control device is configured to form a difference between a measured profile, obtained by measuring a position of the actuation device along the vertical direction during one pump cycle, and a nominal profile prestored in the control device to obtain a difference profile, wherein the control device furthermore is configured to calculate, from the difference profile, a characteristic value for correcting and/or checking pump operation of the infusion device, and wherein an integral of the difference profile along the channel length is formed to obtain the characteristic value.

* * * * *